United States Patent [19]

Schumacher et al.

[11] 4,448,602

[45] May 15, 1984

[54] HERBICIDAL COMPOSITIONS

[75] Inventors: Hans Schumacher, Flörsheim am Main; Konrad Albrecht; Rudolf Heinrich, both of Kelkheim, all of Fed. Rep. of Germany

[73] Assignee: Hoechst Aktiengesellschaft, Frankfurt am Main, Fed. Rep. of Germany

[21] Appl. No.: 418,396

[22] Filed: Sep. 15, 1982

[30] Foreign Application Priority Data

Sep. 17, 1981 [DE] Fed. Rep. of Germany ....... 3136913

[51] Int. Cl.³ .................... A01N 43/02; A01N 43/00
[52] U.S. Cl. ........................................... 71/90; 71/88
[58] Field of Search ...................................... 71/88, 90

[56] References Cited

U.S. PATENT DOCUMENTS 3,904,396  9/1975  Boroschewski et al. .............. 71/111
4,130,413 12/1978  Handte et al. ......................... 71/90
4,336,057  6/1982  Bieringer et al. ..................... 71/88

Primary Examiner—Glennon H. Hollrah
Attorney, Agent, or Firm—Curtis, Morris & Safford

[57] ABSTRACT

Herbicidal compositions containing a compound of the formula I

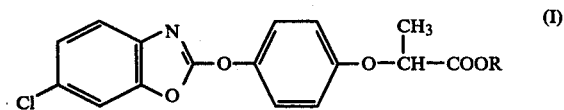

in which R is H, alkyl or a cation equivalent of a base, in combination with a compound of the formula II

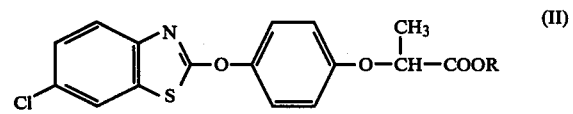

in which R is as defined above, have a selective synergistic herbicidal effect against weed grasses in dicotyledonous crop plants.

6 Claims, No Drawings

HERBICIDAL COMPOSITIONS

Subject of the invention are herbicidal compositions which comprise a compound of the formula I

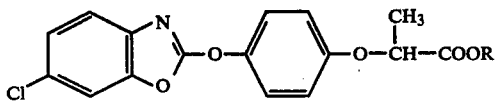

in which R is hydrogen, $(C_1-C_4)$-alkyl or a cation equivalent of an inorganic or organic base, in combination with a compound of the formula II

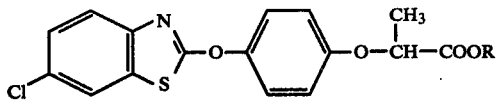

in which R is as defined above.

Preferred compounds of the formulae I and II are those in which R is $C_2H_5$ (compounds Ia and IIa, respectively; compound Ia being ethyl-2-[4-(6-chloro-2-benzoxazolyloxy-phenoxy]propionate, compound IIa being ethyl-2-[4-(6-chloro-2-benzothiazolyloxy)-phenoxy]propionate).

The compounds of the formulae I and II contain asymmetric carbon atoms in their

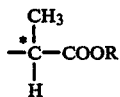

groupings, and they are generally present as racemic mixtures of enantiomer forms (=racemates). The enantiomer forms have a differing biological activity, the compounds of the formulae I and II with D-configuration having an increased activity as compared to the racemates and compounds of L-configuration. In addition to the reacemates, the compositions of the invention comprise furthermore the enantiomer forms of the individual active substances, especially the D-configuration of the compounds of the formulae I and II.

It is known and for example described in German Offenlegungsschrift No. 2,640,730 that the compounds of the formulae I and II when individually applied are especially suitable for selectively combating annual and perennial weed grasses in dicotyledonous crop plants. The compounds of the formula I have for example a good effect in various weed grasses such as *Avena fatua, Digitaria sanguinalis, Echinochloa crus-galli, Eleusine indica, Setaria lutescens* and *Sorghum halepense.*

The compounds of the formula II are for example efficient against *Echinochloa crus-galli, Lolium species, Avena fatua* and crop cereals. Their activity is however insufficient against *Setaria* species, especially *Setaria viridis* and *Setaria lutescens.*

It was therefore the object of the present invention to improve the partially insufficient herbicidal activity on individual application, of the compounds of the formulae I and II and to find an agent having a very good and selective action against an extended scope of annual and perennial weed grasses usually present in cultures of dicotyledonous crop plants.

In accordance with the invention, it has been found that on combined application of compounds of the formula I and compounds of the formula II there is a surprising synergistic herbicidal effect in annual and perennial weed grasses and simultaneously a very high selectivity with respect to dicotyledonous plants.

The herbicidal effect of combinations according to the invention of compounds of the formulae I and II is considerably increased as compared to that of the individual components of the formula I or II, and to the summed effect of these individual components. The combinations of active substances according to the invention can therefore be applied successfully for combating weed grasses, especially for selectively combating mixed annual and perennial grass populations in cultures of dicotyledonous crop plants. In accordance with the invention, the mixing ratio of the components from compounds of the formulae I and II may vary within wide limits of from 10:1 to 1:10. Preferably it is in the range of from 5:1 to 1:5, especially 1:1 to 1:5.

The combinations of active substances according to the invention are especially suitable for combating *Echinochloa crus-galli, Setaria* species, volunteer cereals, *Avena* and *Lolium* species, *Digitaria* and other wild millets in cultures such as rape, beets, flax, onions, lucerne, soybean and other dicotyledonous crop plants. As compared to the individual application of compounds of the formulae I and II, respectively, the combinations of the invention offer the greatest advantage in those cases where the above weed grasses are present as mixed populations which must be controlled.

Active substance combinations of the invention can be applied either as tank mixtures, where the individually formulated active substance components are intermixed immediately before application, or as ready-to-use mixtures. In this latter case they may be formulated as wettable powders, emulsifiable concentrates, dispersions, dusting agents, granules or sprayable solutions, and they optionally contain usual formulation auxiliaries such as wetting agents, emulsifiers, adhesives, dispersing agents, solid or liquid inert substances, carriers, grinding auxiliaries and solvents.

Wettable powders are preparations which can be dispersed homogeneously in water and which, besides the active compound and apart from a diluent or inert substance, if appropriate, also contain wetting agents, for example polyoxyethylated alkylphenols, polyolxyethylated oleyl- or stearylamines, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate or sodium oleoylmethyltauride. Emulsifiable concentrates can be prepared, for example, by dissolving the active compound in an organic solvent, for example butanol, cyclohexanone, dimethylformamide, isophorone or high-boiling aromatic solvents, with the addition of one or more emulsifiers. The following are examples of emulsifiers which can be used: Calcium alkylarylsulfonates, fatty acid polyglycol esters, alkylaryl polyglycol ethers, fatty alcohol polyglycol ethers, polyoxethylated oleyl- or stearylamines, propylene oxide/ethylene oxide condensation products, alkyl polyethers, sorbitan fatty acid esters, alkylaryl/propylene oxide/ethylene oxide condensation products, etc.

Dusting agents can be obtained by grinding the active compound with finely divided solids, for example talc, natural clays, such as kaolin, bentonite or pyrophillite, or diatomaceous earth.

Granules can be prepared either by atomizing a solution of the active compound onto an adsorbent granulated inert material, or by applying active compound concentrates by means of binders, for example polyvinyl alcohol, sodium polyacrylate, methylhydroxyethyl cellulose or mineral oils, to the surface of carriers, such as sand, kaolinite or granulated inert material. Suitable active compound formulations can also be prepared in the manner customary for the production of fertilizer granules—if desired as a mixture with fertilizers.

The synergistic mixtures of active substance from compounds of the formulae I and II according to the invention can be formulated in usual manner, especially as wettable powders, emulsifiable concentrates, solutions, dispersions, dusting agents or granules. The total amount of active substance in the formulations ready to be marketed is about 2 to 95, preferably 5 to 80, weight %, the remainder up to 100% consisting of customary formulation auxiliaries such as adhesives, wetting agents, emulsifiers, dispersing agents, fillers, solvents and carriers.

In wettable powders, the total concentration of active substance from synergistic mixtures of compounds of the formulae I and II varies in a range of from about 10 to 80 weight %, the remainder up to 100 % consisting of usual formulation auxiliaries; in the case of emulsifiable concentrates, it is in a range of about 10 to 70 weight %. Sprayable solutions contain about 2 to 20 weight % of active substance mixture. In the case of granules, the total active substance content is about 2 to 10 weight %, and dust formulations contain about 5 to 20 weight % of active substance mixture.

Subject of the present invention are therefore also herbicidal compositions containing from 2 to 95, preferably 5 to 80, weight % of an active substance combination of compounds of the formulae I and II; the remainder up to 100% consisting of customary formulation auxiliaries.

For application, the concentrates optionally are diluted in a customary manner, for example with water in the case of wettable powders, emulsifiable concentrates and dispersions. Formulations in the form of dust and granules and sprayable solutions are usually not diluted further with other inert substances before use.

Depending on external conditions such as temperature, moisture etc. the required application concentration of the compositions according to the invention varies within wide limits and is generally from 0.1 to 3, preferably 0.2 to 1.5, kg/ha of active substance combination.

The following examples illustrate the invention.

A. FORMULATION EXAMPLES

Examples 1 to 4

Emulsifiable concentrates containing active substance concentrations of the compounds Ia and IIa are obtained from the components listed in the following Table 1 for Examples 1 to 4 by first dissolving the active substance combination at elevated temperature in a mixture of cyclohexanone and xylene, subsequently adding the three emulsifier components with thorough agitation to the solution, and cooling then the resulting mixture to normal temperature with further agitation. In addition to the percentages indicated for the components, Table 1 contains furthermore the proportion of active substance combination in weight % and the weight ratio of compounds Ia: IIa in the active substance combinations.

TABLE 1

| Components | Example No. 1 | 2 | 3 | 4 |
|---|---|---|---|---|
| | Proportion of components in weight % | | | |
| compound Ia | 5 | 6.6 | 10 | 12.75 |
| compound IIa | 15 | 13.4 | 10 | 4.25 |
| cyclohexanone | 30 | 25 | 30 | 30 |
| xylene | 17 | 20 | 17 | 20 |
| fatty alcohol polyglycol ether | 18 | 18 | 18 | 18 |
| oxethylated castor oil | 10 | 9.5 | 9.5 | 9 |
| calcium alkylbenzene sulfonate | 5 | 7.5 | 5.5 | 6 |
| Proportion of compounds Ia + IIa in weight % | 20 | 20 | 20 | 17 |
| weight ratio of compounds Ia:IIa | 1:3 | 1:2 | 1:1 | 3:1 |

B. BIOLOGICAL EXAMPLES

Examples I to V

In the following biological Examples I to V, as to the active substance combinations tested, it is discriminated between the calculated additive effect of the individually applied active substance components and the experimentally found effect of the active substance combinations. The additive effect is calculated according to the formula of S. R. Colby (Calculating synergistic and antagonstic responses of herbicide combinations, Weeds, 15, 1967, pp. 20–22):

$$E = X + Y - X \cdot Y/100,$$

in which
- X = % of damage by herbicide A at x kg/ha of application concentration
- Y = % of damage by herbicide B at y kg/ha of application concentration
- E = expected damage by herbicides A+B at x+y kg/ha of application concentration.

When the actual damage is greater than calculated, the effect of the active substance combination is greater than additive, that is, it is synergistic. This is demonstrated by the following biological Examples I to V. In the corresponding Tables I to V, the right column containing the results of the treatment with the combinations, the additive effect calculated according to the above formula is indicated in brackets after the effect actually obtained.

Test plants of *Lolium multiflorum, Avena fatua, Hordeum vulgare, Digitaria sanguinalis* and *Setaria lutescens*, which were grown separately in planting pots in a greenhouse to the stage of 3 to 4 leaves, were sprayed each in separate post-emergence tests with the individual compounds Ia and IIa in commercial formulations, and with the likewise formulated combinations Ia+IIa, in the form of aqueous spray liquors in the amounts (g of active substance (AS) per hectare) or mixing ratios indicated in Tables I to V, and then placed again in the greenhouse. After 4 weeks, the effect on the test plants (% damage) was determined in comparison to the untreated control plants.

When used individually, a distinct effect becomes manifest after 4 weeks in some cases only. When the active substance combinations according to the invention are applied, the herbicidal effect is substantially good to very good in all cases. A comparison of the additive effect calculated according to the Colby formula and the effect actually found proves that the active substance combinations have a synergistic effect on application. The results of Examples I to V are summarized in the following Tables I to V.

EXAMPLE I

Test plants: *Lolium multiflorum* (rye grass)

TABLE 1

| Treatment with active substance | Dose (g AS/ha) | Effect (% damage) to *Lolium multiflorum* (greenhouse test) after 4 weeks |
|---|---|---|
| Compound I a | 5 | 11 |
|  | 10 | 18 |
| Compound II a | 5 | 43 |
|  | 10 | 67 |
| Compds. Ia + IIa (wt. ratio = 1:1) | 5 | 56 |
|  | 10 | 88 (50) |

EXAMPLE II

Test plants: *Avena fatua* (wild oats)

TABLE II

| Treatment with active substance | Dose (g AS/ha) | Effect (% damage) to *Avena fatua* (greenhouse test) after 4 weeks |
|---|---|---|
| Compound I a | 5 | 0 |
|  | 10 | 10 |
|  | 20 | 38 |
|  | 30 | 47 |
| Compound II a | 5 | 0 |
|  | 10 | 0 |
|  | 20 | 30 |
|  | 30 | 39 |
| Compounds Ia + IIa (wt. ratio = 1:1) | 20 | 46 (10) |
|  | 40 | 70 (57) |
|  | 60 | 90 (68) |

EXAMPLE III

Test plants: *Hordeum vulgare* (barley)

TABLE III

| Treatment with active substance | Dose (g AS/ha) | Effect (% damage) to *Hordeum vulgare* (greenhouse test) after 4 weeks |
|---|---|---|
| Compound I a | 5 | 0 |
|  | 10 | 0 |
|  | 15 | 0 |
|  | 20 | 10 |
|  | 30 | 18 |
| Compound II a | 5 | 10 |
|  | 10 | 33 |
|  | 15 | 56 |
|  | 20 | 68 |
|  | 30 | 86 |
| Compounds Ia + IIa (wt. ratio = 1:1) | 20 | 73 (33) |
|  | 30 | 91 (56) |
|  | 40 | 97 (72) |
| Compounds Ia + IIa (wt. ratio = 1:2) | 30 | 93 (68) |
| Compounds Ia + IIa (wt. ratio = 1:3) | 20 | 77 (56) |

EXAMPLE IV

Test plants: *Digitaria sanguinalis* (crabgrass)

TABLE IV

| Treatment with active substance | Dose (g AS/ha) | Effect (% damage) to *Digitaria sanguinalis* (greenhouse test) after 4 weeks |
|---|---|---|
| Compound I a | 5 | 59 |
|  | 10 | 94 |
| Compound II a | 5 | 0 |
|  | 10 | 0 |
|  | 20 | 7 |
| Compounds Ia + IIa (wt. ratio = 1:1) | 10 | 95 (59) |
| Compounds Ia + IIa (wt. ratio = 1:2) | 30 | 100 (95) |

EXAMPLE V

Test plants: *Setaria lutescens* (yellow foxtail)

TABLE V

| Treatment with active substances | Dose (g AS/ha) | Effect (% damage) to *Setaria lutescens* (greenhouse test) after 4 weeks |
|---|---|---|
| Compound I a | 5 | 60 |
|  | 10 | 82 |
| Compound II a | 5 | 7 |
|  | 10 | 10 |
|  | 20 | 11 |
| Compounds Ia + IIa (wt. ratio = 1:1) | 10 | 84 (63) |
|  | 20 | 88 (84) |
| Compounds Ia + IIa (wt. ratio = 1:2) | 30 | 92 (84) |

What is claimed is:

1. A herbicidal composition consisting essentially of an effective amount of the mixture of a compound of the formula I

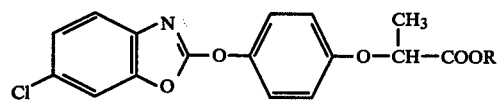

in which R is $(C_1-C_4)$-alkyl, in combination with a compound of the formula II

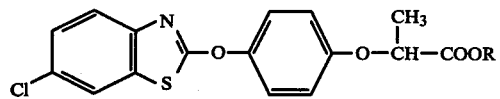

in which R is as defined above, the mixing ratio of compounds of the formulae I and II being from 1:1 to 1:5.

2. The herbicidal composition, as claimed in claim 1, in which R is ethyl.

3. The herbicidal composition as claimed in claim 1, which comprises from 2 to 95 weight % of an active substance combination of compounds of the formulae I and II, the remainder up to 100% consisting of inert carriers.

4. The herbicidal composition, as claimed in claim 1 containing 5 to 80 weight % of an active substance combination of compounds of the formulae I and II.

5. A process for combating weeds by postemergence treatment which comprises applying to areas infested therewith herbicidal compositions as claimed in any one of claims 1 to 4 in amounts corresponding to 0.1 to 3 kg/ha of active substance combination.

6. A process for combating weeds which comprises the postemergence treatment of areas of dicotyledonous crop plants infested with annual and perennial grass with an effective amount of a herbicidal composition as claimed in any one of claims 8 to 11.

* * * * *